US006544743B1

(12) United States Patent
Hudson et al.

(10) Patent No.: US 6,544,743 B1
(45) Date of Patent: Apr. 8, 2003

(54) PEROXISOME PROLIFERATOR-ACTIVATED RECEPTOR ALPHA AND DISORDERS OF LIPID METABOLISM

(75) Inventors: Thomas J. Hudson, Westmount (CA); Marie-Claude Vohl, Cap-Rouge (CA); Carl Brewer, Montreal (CA); Kenneth Morgan, Montreal (CA); Daniel Gaudet, Chicoutimi (CA)

(73) Assignees: McGill University, Montreal (CA); Complexe Hospitalier de la Sagamie, Chicoutimi (CA)

( * ) Notice: Subject to any disclaimer, the term of this patent is extended or adjusted under 35 U.S.C. 154(b) by 0 days.

(21) Appl. No.: 09/662,386

(22) Filed: Sep. 14, 2000

Related U.S. Application Data
(60) Provisional application No. 60/154,736, filed on Sep. 17, 1999.

(51) Int. Cl.[7] .......................... C12Q 1/68; C12P 19/34; C07H 21/02; C07H 21/04

(52) U.S. Cl. ..................... 435/6; 435/91.2; 536/23.5; 536/24.31; 536/24.33

(58) Field of Search ................ 435/6, 91.2; 536/23.5, 536/24.31, 24.33

(56) References Cited

PUBLICATIONS

D. Evans et al., A polmorphism, L162V in the peroxisome proliferator–activated receptor . . . , May 2001, Springer–Verlag 2001, Original Article, pp. 198–204.*

C. Lacquemant et al., Mutation Screening of the PPARa Gene in Type 2 Diabetes Assoc. with Coronary Heart Disease, Diabetes & Metabolism(Paris) May 2000, vol. 26, pp. 393–401.*

Isseman, I, et al., "Activation of a Member of the Steroid Hormone Receptor Superfamily by Peroxisome Proliferators," *Nature*, 347:645–650 (1990).

Kliewer, S., et al., "Fatty Acids and Eicosanoids Regulate Gene Expression Through Direct Interactions with Peroxisome Proliferator–Activated Receptors α and γ," *Proc. Natl. Acad. Sci.*, 94:4318–4323 (1997).

Pineda–Torra, I., et al., "Peroxisome Proliferator–Activated Receptor Alpha in Metabolic Disease, Inflammation, Atherosclerosis and Aging," *Current Opinion in Lipidology*, 10:151–159 (1999).

Djouadi, F., et al., "The Role of the Peroxisome Proliferator–Activated Receptor α (PPARα) in the Control of Cardiac Lipid Metabolism," *Prostaglandins, Leukotrienes & Essential Fatty Acids*, 60(5–6):339–343 (1999).

Vohl, M.C., et al., "Molecular Scanning of the Human PPARα Gene: Association of the L162V Mutation with Hyperapobetalipoproteinemia," *J. of Lipid Res.*, 41:945–952 (2000).

Peters, J.M., et al., "Alterations in Lipoprotein Metabolism in Peroxisome Proliferator–Activated Receptor α–Deficient Mice," *J. of Biological Chem.*, 272(43):27307–27312 (1997).

Flavell, D.M., et al., "Variation in the PPARα Gene is Associated with Altered Function In Vitro and Plasma Lipid Concentrations in Type II Diabetic Subjects," *Diabetologia*, 43:673–680 (2000).

Sher, T., et al., "cDNA Cloning, Chromosomal Mapping, and Functional Characterization of the Human Peroxisome Proliferator Activated Receptor," *Biochemistry*, 32:5598–5604 (1993).

Schoonjans, K., et al., "Peroxisome Proliferator–Activated Receptors, Orphans with Ligands and Functions," *Current Opinion in Lipidology*, 8:159–166 (1997).

Schoonjans, K., et al., "The Peroxisome Proliferator Activated Receptors (PPARs) and their Effects on Lipid Metabolism and Adipocyte Differentiation," *Biochimica et Biophysica Acta*, 1302:93–109 (1996).

Schoonjans, K., et al, "Role of the Peroxisome Proliferator–Activated Receptor (PPAR) in Mediating the Effects of Fibrates and Fatty Acids on Gene Expression," *J. of Lipid Res.*, 37:907–925 (1996).

Vidal–Puig, A., et al., "Peroxisome Proliferator–Activated Receptor Gene Expression in Human Tissues," *J. Clin. Invest.*, 99(10):2416–2422 (1997).

Brun, R.P., et al., "Differential Activation of Adipogenesis by Multiple PPAR Isoforms," *Genes & Development*, 10:974–984 (1996).

Auboeuf, D., et al., "Tissue Distributiion and Quantification of the Expression of mRNAs of Peroxisome Proliferator–Activated Receptors and Liver X Receptor–α in Humans," *Diabetes*, 46:1319–1327 (1997).

Inoue, I., et al., "The Peroxisome Proliferator–Activated Receptor α (PPARα) Regulates the Plasma Thiobarbituric Acid–Reactive Substance (TBARS) Level," *Biochem. and Biophys. Res. Comm.*, 237:606–610 (1997).

Horrobin, D.F., "Abnormal Membrane Concentrations of 20 and 22–Carbon Essential Fatty Acids: A Common Link Between Risk Factors and Coronary and Peripheral Vascular Disease?", *Prostaglandins Leukotrienes and Essential Fatty Acids*, 53:385–396 (1995).

Djouadi, F., et al., "A Gender–Related Defect in Lipid Metabolism and Glucose Homeostasis in Peroxisome Proliferator–Activated Receptor α–Deficient Mice," *J. Clinical Investigation*, 102(6): 1083–1091 (1998).

(List continued on next page.)

Primary Examiner—Carla J. Myers
(74) Attorney, Agent, or Firm—Hamilton, Brook, Smith & Reynolds, P.C.

(57) ABSTRACT

The complete genomic structure of the peroxisome proliferator-activated receptor alpha gene is described. Also described are the identification of novel single nucleotide polymorphisms and association with higher plasma LDL-cholesterol and total and LDL-apolipoprotein B concentrations.

8 Claims, 3 Drawing Sheets

OTHER PUBLICATIONS

Ruotolo, G., et al., "Treatment Effects on Serum Lipoprotein Lipids, Apolipoproteins and Low Density Lipoprotein Particle Size and Relationships of Lipoprotein Variables to Progression of Coronary Artery Disease in the Bezafibrate Coronary Athersoclerosis Intervention Trial (BECAIT)", *J. Am. Coll. Cardiol.*, 32(6):1648–1656 (1998).

Bell, A.R., et al., "Molecular Basis of Non–Responsiveness to Peroxisome Proliferators: the Guinea–Pig PPARα is Functional and Mediates Peroxisome Proliferator–Induced Hypolipidaemia," *Biochem. J.*, 332:689–693 (1998).

* cited by examiner

```
ggcccaggct gaagctcagg gccctgtctg ctctgtggac tcaacagttt gtggcaagac  61
aagctcagaa ctgagaagct gtcaccacag ttctggaggc tgggaagttc aagatcaaag 121
tgccagcaga ttcagtgtca tgtgaggacg tgcttcctgc ttcatagata agagcttgga 181
gctcggcgca caaccagcac catctggtcg cgatggtgga cacggaaagc ccactctgcc 241
ccctctcccc actcgaggcc ggcgatctag agagcccgtt atctgaagag ttcctgcaag 301
aaatgggaaa catccaagag atttcgcaat ccatcggcga ggatagttct ggaagctttg 361
gctttacgga ataccagtat ttaggaagct gtcctggctc agatggctcg gtcatcacgg 421
acacgctttc accagcttcg agcccctcct cggtgactta tcctgtggtc cccggcagcg 481
tggacgagtc tcccagtgga gcattgaaca tcgaatgtag aatctgcggg gacaaggcct 541
caggctatca ttacggagtc cacgcgtgtg aaggctgcaa gggcttcttt cggcgaacga 601
ttcgactcaa gctggtgtat gacaagtgcg accgcagctg caagatccag aaaaagaaca 661
gaaacaaatg ccagtattgt cgatttcaca agtgcctttc tgtcgggatg tcacacaacg 721
cgattcgttt tggacgaatg ccaagatctg agaaagcaaa actgaaagca gaaattctta 781
cctgtgaaca tgacatagaa gattctgaaa ctgcagatct caaatctctg gccaagagaa 841
tctacgaggc ctacttgaag aacttcaaca tgaacaaggt caaagcccgg tcatcctct 901
caggaaaggc cagtaacaat ccaccttttg tcatacatga tatggagaca ctgtgtatgg 961
ctgagaagac gctggtggcc aagctggtgg ccaatggcat ccagaacaag gaggcggagg 1021
tccgcatctt tcactgctgc cagtgcacgt cagtggagac cgtcacggag ctcacggaat 1081
tcgccaaggc catcccaggc ttcgcaaact tggacctgaa cgatcaagtg acattgctaa 1141
aatacggagt ttatgaggcc atattcgcca tgctgtcttc tgtgatgaac aaagacggga 1201
tgctggtagc gtatggaaat gggtttataa ctcgtgaatt cctaaaaagc taaggaaac 1261
cgttctgtga tatcatggaa cccaagtttg attttgccat gaagttcaat gcactggaac 1321
tggatgacag tgatatctcc ctttttgtgg ctgctatcat ttgctgtgga gatcgtcctg 1381
gccttctaaa cgtaggacac attgaaaaaa tgcaggaggg tattgtacat gtgctcagac 1441
tccacctgca gagcaaccac ccggacgata tctttctctt cccaaaactt cttcaaaaaa 1501
tggcagacct ccggcagctg gtgacggagc atgcgcagct ggtgcagatc atcaagaaga 1561
cggagtcgga tgctgcgctg cacccgctac tgcaggagat ctacagggac atgtactgag 1621
ttccttcaga tcagccacac cttttccagg agttctgaag ctgacagcac tacaaaggag 1681
acggggagc agcacgattt tgcacaaata tccaccactt taaccttaga gcttggacag 1741
tctgagctgt aggtaaccgg catattattc catatctttg ttttaaccag tacttctaag 1801
agcatagaac tcaaatgctg ggggaggtgg ctaatctcag gactgggaag (SEQ ID NO: 1)
```

Figure 2

MVDTESPLCPLSPLEAGDLESPLSEEFLQEMGNIQEISQSIGEDSSGSFGFTEYQYLGSCPGSDGSVITDTLSPA
SSPSSVTYPVVPGSVDESPSGALNIECRICGDKASGYHYGVHACEGCKGFFRRTIRLKLVYDKCDRSCKIQK
KNRNKCQYCRFHK CLSVGMSHNAIRFGRMPRSEKAKLKAEILTCEHDIEDSETADLKSLAKRIYEAYLKNF
NMNKVKARVILSGKASNNPPFVIHDMETLCMAEKTLVAKLVANGIQNKEAEVRIFHCCQCTSVETVTELTE
FAKAIPGFANLDLNDQVTLLKYGVYEAIFAMLSSVMNKDGMLVAYGNGFITREFLKSLRKPFCDIMEPKFD
FAMKFNALELDDSDISLFVAAIICCGDRPGLLNVGHIEKMQEGIVHVLRLHLQSNHPDDIFLFPKLLQKMAD
LRQLVTEHAQLVQIIKKT ESDAALHPLLQEIYRDMY (SEQ ID NO: 2)

Figure 3

PEROXISOME PROLIFERATOR-ACTIVATED RECEPTOR ALPHA AND DISORDERS OF LIPID METABOLISM

RELATED APPLICATIONS

This application claims the benefit of U.S. Provisional application Serial No. 60/154,736, filed Sep. 17, 1999, the entire teachings of which are incorporated herein by reference.

BACKGROUND OF THE INVENTION

Peroxisome proliferator-activated receptors (PPARs) are members of a large family of ligand-inducible transcription factors that includes receptor for retinoids and vitamin D as well as thyroid and steroid hormones (1). PPARs regulate the expression of target genes by binding to DNA sequence elements, termed PPAR response elements (PPRE) (2,3). PPREs have been identified in the regulatory regions of a variety of genes involved in lipid and energy balance. Three different PPAR genes have been identified ($\alpha$, $\delta$ and $\gamma$) (2,3). PPAR$\gamma$, expressed mainly in adipose tissue, regulates adipocyte differentiation (4,5). PPAR$\alpha$, the first to be identified, is expressed mainly in tissues that have a high level of fatty acid (FA) catabolism such as the liver, kidney, heart and muscle (6,7). Numerous studies have demonstrated that several genes encoding enzymes involved in $\beta$ and $\omega$-oxidation are under the control of PPAR$\alpha$ (2,3). PPAR$\alpha$ is activated by medium and very long chain FA and polyunsaturated FA, such as eicosapentaenoic acid (8). In addition to its role in FA oxidation, PPAR$\alpha$ appears to play an important role in the control of extracellular lipid metabolism. In fact, a variety of hypolipidemic fibrates are synthetic ligands for PPAR$\alpha$ (9).

FAs are essential biological components and are used as metabolic fuels, covalent regulators of signaling molecules, and essential components of cellular membranes. Thus, FA must be kept within narrow physiological limits. Altered levels of FA are linked to a variety of metabolic diseases including atherosclerosis, hyperlipidemia, obesity, insulin resistance and type 2 diabetes (10, 11).

SUMMARY OF THE INVENTION

Peroxisome proliferator-activated receptor alpha (PPAR$\alpha$) is a member of the steroid hormone receptor super family that is involved in the control of cellular lipid utilization. As described herein, the genomic structure of the human PPAR$\alpha$ was determined, and intronic primers were designed to sequence the complete coding region and the exon-intron boundaries of the human PPAR$\alpha$ gene among 12 patients with type 2 diabetes and 2 controls. Sequence analyses revealed the presence of a L162V missense mutation in exon 5; that is, there is a C to G transversion in the first position of codon 162 leading to a substitution of a valine for the leucine at that position. Mutation L162V is contained within the DNA binding domain of the human PPAR$\alpha$ gene, and leucine 162 is highly conserved among humans, mice, rats and guinea pigs. Among diabetics and controls, a trend was observed toward higher plasma LDL-cholesterol and apolipoprotein B levels among carriers of the rare V162 allele. To verify these findings, an independent cohort of 193 non-diabetic subjects recruited in the greater Quebec City area was screened. Comparison of the lipoprotein-lipid profile between L162 homozygotes and carriers of the rare V 162 allele showed significant differences in plasma LDL-cholesterol, total and LDL-apolipoprotein B concentrations, carriers of the V 162 allele having the highest levels. These results suggest that the rare V162 allele may make the subjects more prone to develop a hyperapobetalipoproteinemia.

Thus, the invention relates to the SNPs identified as described herein, both singly and in combination, as well as to the use of these SNPs, and others in PPAR (e.g., PPAR$\alpha$) genes, particularly those nearby in linkage disequilibrium with these SNPs, for diagnosis, prediction of clinical course and treatment response for disorders of lipid metabolism, development of new treatments for disorders of lipid metabolism based upon comparison of the variant and normal versions of the gene or gene product, and development of cell-culture based and animal models for research and treatment of disorders of lipid metabolism. The invention also relates to methods for diagnosing and treating disorders of lipid metabolism, especially high LDL cholesterol levels and hyperapobetalipoproteinemias, and to methods for identifying compounds for use in the diagnosis and treatment of said disorders. The invention further relates to novel compounds and pharmaceutical compositions for use in the diagnosis and treatment of disorders of lipid metabolism.

The invention relates to isolated nucleic acid molecules comprising all or a portion of the variant allele of PPAR$\alpha$ (e.g., wherein reference or wildtype PPAR$\alpha$ is exemplified by SEQ ID NO: 1). Preferred portions are at least 10 contiguous nucleotides and comprise the polymorphic site, e.g., a portion of SEQ ID NO: 1 which is at least 10 contiguous nucleotides and comprises the "G" at the first position of codon 162 (nucleotide 696) of the PPAR$\alpha$ gene, or a portion of SEQ ID NO: 1 which is at least 10 contiguous nucleotides and comprises the "A" at the last position of codon 253 (nucleotide 971) of the PPAR$\alpha$ gene. The invention further relates to isolated gene products, e.g., polypeptides or proteins, which are encoded by a nucleic acid molecule comprising all or a portion of the variant allele of PPAR$\alpha$.

The invention further relates to isolated proteins or polypeptides comprising all or a portion of the variant amino acid sequence of PPAR$\alpha$ (e.g., wherein reference or wildtype PPAR$\alpha$ is exemplified by SEQ ID NO: 2), and to isolated proteins or polypeptides comprising all or a portion of the variant amino acid sequence of PPAR$\alpha$. Preferred polypeptides are at least 10 contiguous amino acids and comprise the polymorphic amino acid, e.g., a portion of SEQ ID NO: 2 which is at least 10 contiguous amino acids and comprises the valine at residue 162. The invention further relates to isolated nucleic acid molecules encoding such proteins and polypeptides, as well as to antibodies which bind, e.g., specifically, to such proteins and polypeptides.

In one embodiment, the invention relates to a method for predicting the likelihood that an individual will have a disorder of lipid metabolism (or diagnosing or aiding in the diagnosis of a disorder of lipid metabolism), e.g., high LDL cholesterol levels, atherosclerosis, coronary heart disease and/or hyperapobetalipoproteinemias, comprising the steps of obtaining a DNA sample from an individual to be assessed and determining the nucleotide present at the first position of codon 162 (nucleotide 696) of the PPAR$\alpha$ gene. The presence of a "C" (the reference nucleotide) at this position indicates that the individual has a lower likelihood of having a disorder of lipid metabolism than an individual having a "G" at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia.

In a particular embodiment, the individual is an individual at risk for development of a disorder of lipid metabolism.

In another embodiment, the invention relates to a method for predicting the likelihood that an individual will have a disorder of lipid metabolism (or diagnosing or aiding in the diagnosis of a disorder of lipid metabolism), e.g., high LDL cholesterol levels, atherosclerosis, coronary heart disease and/or hyperapobetalipoproteinemias, comprising the steps of obtaining a DNA sample from an individual to be assessed and determining the nucleotide present at the first position of codon 162 (nucleotide 696) of the PPARα gene. The presence of a "G" (the variant nucleotide) at this position indicates that the individual has a greater likelihood of having a disorder of lipid metabolism than an individual having a "C" at that position, or a greater likelihood of having more severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of a disorder of lipid metabolism.

In another embodiment, the invention relates to a method for predicting the likelihood that an individual will have a disorder associated with a "G" at nucleotide position 696 of the PPARα gene (or diagnosing or aiding in the diagnosis of such a disorder) comprising the steps of obtaining a DNA sample from an individual to be assessed and determining the nucleotide present at position 696 of the PPARα gene. The presence of a "G" at this position indicates that the individual has a greater likelihood of having a disorder associated therewith than an individual having a "C" at that position, or a greater likelihood of having more severe symptomology. Conversely, the presence of a "C" at this position indicates that the individual has a lower likelihood of having a disorder associated therewith than an individual having a "G" at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of such a disorder.

In another embodiment, the invention relates to a method for predicting the likelihood that an individual will have a disorder associated with a "C" at nucleotide position 696 of the PPARα gene (or diagnosing or aiding in the diagnosis of such a disorder) comprising the steps of obtaining a DNA sample from an individual to be assessed and determining the nucleotide present at position 696 of the PPARα gene. The presence of a "C" at this position indicates that the individual has a greater likelihood of having a disorder associated therewith than an individual having a "G" at that position, or a greater likelihood of having more severe symptomology. Conversely, the presence of a "G" at this position indicates that the individual has a lower likelihood of having a disorder associated therewith than an individual having a "G" at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of such a disorder.

In another embodiment, the invention relates to a method for predicting the likelihood that an individual will have a disorder associated with an "A" at nucleotide position 971 of the PPARα gene (or diagnosing or aiding in the diagnosis of such a disorder) comprising the steps of obtaining a DNA sample from an individual to be assessed and determining the nucleotide present at position 971 of the PPARα gene. The presence of an "A" at this position indicates that the individual has a greater likelihood of having a disorder associated therewith than an individual having a "G" at that position, or a greater likelihood of having more severe symptomology. Conversely, the presence of a "G" at this position indicates that the individual has a lower likelihood of having a disorder associated therewith than an individual having a "A" at that position, or a greater likelihood of having less severe symptomology. In a particular embodiment, the individual is an individual at risk for development of such a disorder.

In another embodiment, the invention relates to a method for predicting the likelihood that an individual will have a disorder associated with a "G" at nucleotide position 971 of the PPARα gene (or diagnosing or aiding in the diagnosis of such a disorder) comprising the steps of obtaining a DNA sample from an individual to be assessed and determining the nucleotide present at position 971 of the PPARα gene. The presence of a "G" at this position indicates that the individual has a greater likelihood of having a disorder associated therewith than an individual having a "A" at that position, or a greater likelihood of having more severe symptomology. Conversely, the presence of an "A" at this position indicates that the individual has a lower likelihood of having a disorder associated therewith than an individual having a "G" at that position, or a greater likelihood of having less severe symptomology. In a particular embodiment, the individual is an individual at risk for development of such a disorder.

In one embodiment, the invention relates to a method for predicting the likelihood that an individual will have a disorder of lipid metabolism (or diagnosing or aiding in the diagnosis of a disorder of lipid metabolism), e.g., high LDL cholesterol levels, atherosclerosis, coronary heart disease and/or hyperapobetalipoproteinemias, comprising the steps of obtaining a biological sample comprising the PPARα protein or relevant portion thereof from an individual to be assessed and determining the amino acid present at amino acid position 162 of the PPARα protein. The presence of a leucine (the reference amino acid) at this position indicates that the individual has a lower likelihood of having a disorder of lipid metabolism than an individual having a valine at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of a disorder of lipid metabolism.

In another embodiment, the invention relates to a method for predicting the likelihood that an individual will have a disorder of lipid metabolism (or diagnosing or aiding in the diagnosis of a disorder of lipid metabolism), e.g., high LDL cholesterol levels, atherosclerosis, coronary heart disease and/or hyperapobetalipoproteinemias, comprising the steps of obtaining a.biological sample comprising the PPARα protein or relevant portion thereof from an individual to be assessed and determining the amino acid present at amino acid position 162 of the PPARα protein. The presence of a valine (the variant amino acid) at this position indicates that the individual has a greater likelihood of having a disorder of lipid metabolism than an individual having a leucine at that position, or a greater likelihood of having more severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of a disorder of lipid metabolism.

In another embodiment, the invention relates to a method for predicting the likelihood that an individual will have a disorder associated with a valine at amino acid position 162 of the PPARα protein (or diagnosing or aiding in the diagnosis of such a disorder) comprising the steps of obtaining a biological sample comprising the PPARα protein or relevant portion thereof from an individual to be assessed and determining the amino acid present at amino acid position 162 of the PPARα protein. The presence of a valine at this position indicates that the individual has a greater likelihood of having a disorder associated therewith than an individual having a leucine at that position, or a greater likelihood of having more severe symptomology. Conversely, the presence of a leucine at this position indicates that the individual has a lower likelihood of having a disorder associated therewith than an individual having a valine at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of such a disorder.

In another embodiment, the invention relates to a method for predicting the likelihood that an individual will have a disorder associated with a leucine at amino acid position 162 of the PPARα protein (or diagnosing or aiding in the diagnosis of such a disorder) comprising the steps of obtaining a biological sample comprising the PPARα protein or relevant portion thereof from an individual to be assessed and determining the amino acid present at amino acid position 162 of the PPARα protein. The presence of a leucine at this position indicates that the individual has a greater likelihood of having a disorder associated therewith than an individual having a valine at that position, or a greater likelihood of having more severe symptomology. Conversely, the presence of a valine at this position indicates that the individual has a lower likelihood of having a disorder associated therewith than an individual having a leucine at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of such a disorder.

In another embodiment, the invention relates to pharmaceutical compositions comprising a reference or variant PPARα gene or gene product, or biologically active portion thereof. The invention relates to pharmaceutical compositions comprising a reference PPARα gene or gene product, or biologically active portion thereof for use in the treatment of lipid metabolism disorders. The invention further relates to the use of compositions (i.e., agonists and antagonists) which enhance or increase or which reduce or decrease, respectively, the activity of a PPARα gene product for use in the treatment of disorders of lipid metabolism.

BRIEF DESCRIPTION OF THE DRAWING

FIG. 2 shows a nucleotide sequence (SEQ ID NO: 1) of the PPARα mRNA.

FIG. 3 shows an amino acid sequence (SEQ ID NO: 2) of the PPARα protein.

DETAILED DESCRIPTION OF THE INVENTION

Figure 1:
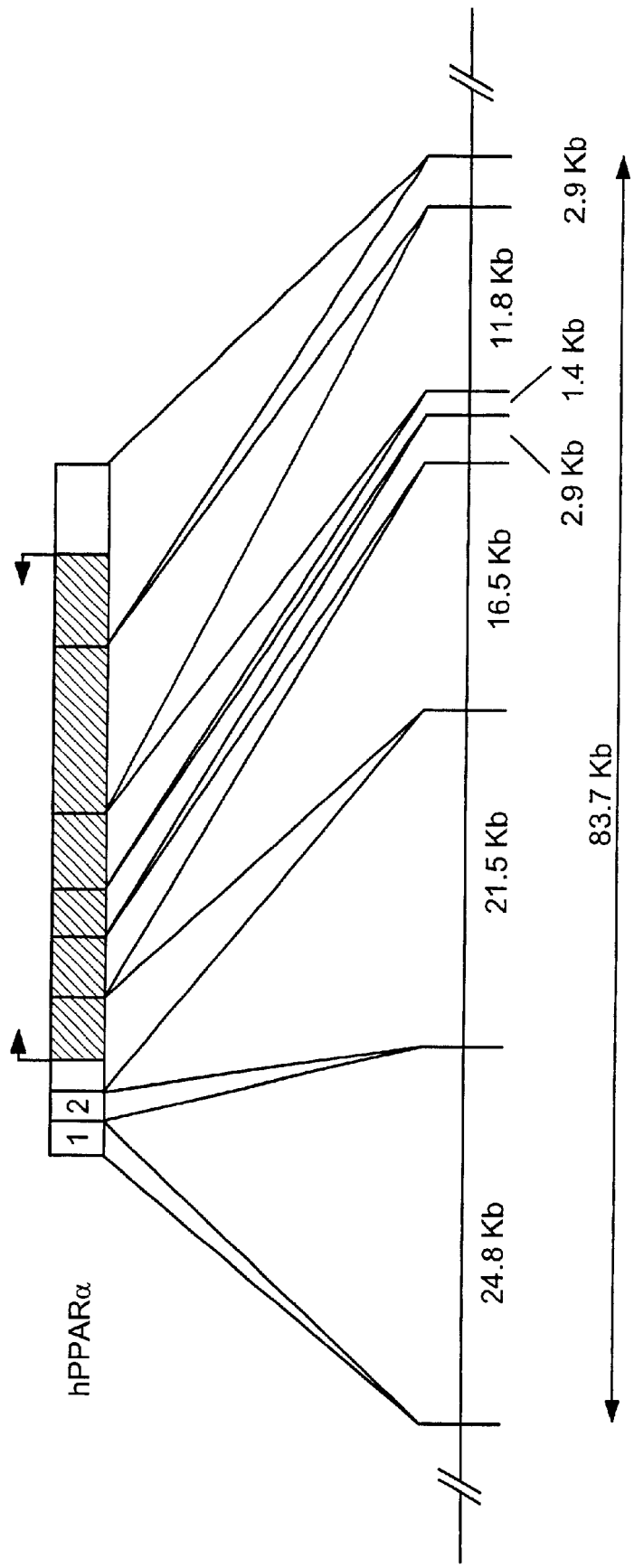
FIG. 1 shows a schematic representation of the human PPARα gene. The upper portion is a representation of the human PPARα messenger RNA. The coding region is shaded and arrows indicate initiator and stop codons. The spatial localization of exons within the gene is shown in the lower portion. Intron sizes are also indicated. The gene spans 83.7 Kb of genomic DNA.

A list of references referred to herein by number can be found at the end of the Specification.

The human PPARα gene has been mapped on chromosome 22 slightly telomeric to a linkage group of six genes and genetic markers located in the region 22q 12-q 13.1 (24). As described herein, the structure of the human PPARα gene has been determined. This will facilitate genetics studies evaluating the role of this gene in insulin resistance, type 2 diabetes and dyslipidemia. The human gene spans about 83.7 Kb and is composed of 8 exons. The 5' donor and 3' acceptor splice sites were found to be in agreement to the consensus splice donor and acceptor sequences. The position of introns separating coding exons is conserved between the human and mouse genes (25). However, the sequence of the non-coding portion of the gene shows no significant homology across the two species (24,25). It has been observed that the expression of PPARα mRNA in liver is significantly lower in humans (26,27).

As described herein, direct sequencing of the entire coding region of the human PPARα gene as well as exon-intron boundaries revealed the presence of a silent G to A substitution in exon 7 (nucleotide 971 of the PPARα gene). This substitution does not contribute to an amino acid change, as both polymorphic forms encode a threonine at amino acid position 253, but is considered part of the subject application; for example, this polymorphism can be used to genotype PPARα or in a diagnostic method for disorders associated with one or the other allele. Sequence analyses also revealed the presence of a L162V missense mutation (polymorphism) in exon 5; that is, there is a C to G transversion in the first position of codon 162 (nucleotide 696), leading to a substitution of a valine for a leucine at amino acid 162. In this instance, "C" is considered the reference nucleotide and "G" is considered the variant nucleotide.

As used herein, polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair, in which case it is referred to as a single nucleotide polymorphism.

The contribution of the L162V missense mutation to the modulation of the lipoprotein-lipid profile was examined. A trend toward higher LDL-cholesterol and plasma total-apolipoprotein B levels was seen among carriers of the V162 allele of the diabetes case-control cohort. The use of a Quebec City non-diabetic male cohort confirmed this tendency, as carriers of the V162 allele had the highest LDL-cholesterol, total and LDL-apolipoprotein B levels. The presence of the V162 allele was associated with a 10.6, 10.3 and 11.7% increase in plasma LDL-cholesterol, total and LDL-apolipoprotein B levels, respectively. These results suggest that the PPARα L162V missense mutation may modulate the concentration of apolipoprotein B-containing lipoproteins. Thus, carriers of the rare V162 allele may be more prone to develop atherosclerosis and subsequent coronary heart disease, since increased levels of LDL-cholesterol and apolipoprotein B levels are well known risk factors for heart disease (28–31).

Thus, it is possible that changes in PPARα activity could contribute to the observed lipoprotein-lipid variability in the population. Results presented herein suggest that the L162V mutation may modulate plasma lipoprotein-lipid levels. This missense mutation results in a non-conservative amino acid substitution located within the DNA binding domain or C domain of the protein (26). This domain, which targets the receptor to specific DNA sequences known as hormone response element (HRE) or PPRE for PPAR specific genes, is the most conserved among nuclear receptor domains, (2,3,26). Taken together, these observations suggest that the leucine 162 may be important for the activity of PPARα and thus the valine substitution may alter its activity. It is also possible that the L162V mutation is in linkage disequilibrium with a functional mutation in another gene in the neighborhood that regulates blood lipid concentrations.

The invention relates to isolated nucleic acid molecules comprising all or a portion of the variant allele of PPARα (e.g., wherein reference or wildtype PPARα is exemplified by SEQ ID NO: 1). Preferred portions are at least 10 contiguous nucleotides and comprise the polymorphic site, e.g., a portion of SEQ ID NO: 1 which is at least 10 contiguous nucleotides and comprises the "G" at the first position of codon 162 (nucleotide 696) of the PPARα gene, or a portion of SEQ ID NO: 1 which is at least 10 contiguous nucleotides and comprises the "A" at the last position of codon 253 (nucleotide 971) of the PPARα gene. The invention further relates to isolated gene products, e.g., polypeptides or proteins, which are encoded by a nucleic acid molecule comprising all or a portion of the variant allele of PPARα.

A nucleic acid molecule or oligonucleotide can be DNA or RNA, and single- or double-stranded. Nucleic acid molecules and oligonucleotides can be naturally occurring or synthetic, but are typically prepared by synthetic means. Preferred nucleic acid molecules and oligonucleotides of the invention include segments of DNA, or their complements, which include any one of the polymorphic sites shown in the Table. The segments can be between 5 and 250 bases, and, in specific embodiments, are between 5–10, 5–20, 10–20, 10–50, 20–50 or 10–100 bases. For example, the segment can be 21 bases. The polymorphic site can occur within any position of the segment.

The invention also relates to nucleic acid molecules which hybridize to the variant alleles identified herein (or their complements) and which also comprise the variant nucleotide at the SNP site. Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

The invention also relates to nucleic acid molecules which share substantial sequence identity to the variant alleles identified herein (or their complements) and which also comprise the variant nucleotide at the SNP site. Particularly preferred are nucleic acid molecules and fragments which have at least about 60%, preferably at least about 70, 80 or 85%, more preferably at least about 90%, even more preferably at least about 95%, and most preferably at least about 98% identity with nucleic acid molecules described herein. The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of a sequence aligned for comparison purposes is at least 30%, preferably at least 40%, more preferably at least 60%, and even more preferably at least 70%, 80% or 90% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA*, 90:5873–5877 (1993). Such an algorithm is incorporated into the NBLAST and XBLAST programs (version 2.0) as described in Altschul et al., *Nucleic Acids Res.*, 25:389–3402 (1997). When utilizing BLAST and Gapped BLAST programs, the default parameters of the respective programs (e.g., NBLAST) can be used. See http://www.ncbi.nlm.nih.gov. In one embodiment, parameters for sequence comparison can be set at score=100, wordlength=12, or can be varied (e.g., W=5 or W=20).

The term "isolated" is used herein to indicate that the material in question exists in a physical milieu distinct from that in which it occurs in nature. For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Preferably, an isolated nucleic acid comprises at least about 50, 80 or 90 percent (on a molar basis) of all macromolecular species present. Thus, the invention relates to a method for predicting the likelihood that an individual will have a disorder of lipid metabolism (or diagnosing or aiding in the diagnosis of a disorder of lipid metabolism), e.g., high LDL cholesterol levels, atherosclerosis, coronary heart disease and/or hyperapobetalipoproteinemias, comprising the steps of obtaining a DNA sample from an individual to be assessed and determining the nucleotide present at the first position of codon 162 (nucleotide 696) of the PPARα gene. The presence of a "C" (the reference nucleotide) at this position indicates that the individual has a lower likelihood of having a disorder of lipid metabolism than an individual having a "G" at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of a disorder of lipid metabolism.

In another embodiment, the invention relates to a method for predicting the likelihood that an individual will have a disorder of lipid metabolism (or diagnosing or aiding in the diagnosis of a disorder of lipid metabolism), e.g., high LDL cholesterol levels, atherosclerosis, coronary heart disease and/or hyperapobetalipoproteinemias, comprising the steps of obtaining a DNA sample from an individual to be assessed and determining the nucleotide present at the first position of codon 162 (nucleotide 696) of the PPARα gene. The presence of a "G" (the variant nucleotide) at this position indicates that the individual has a greater likelihood of having a disorder of lipid metabolism than an individual having a "C" at that position, or a greater likelihood of having more severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of a disorder of lipid metabolism.

As used herein, disorders of lipid metabolism include, but are not limited to, abnormal lipoprotein-lipid variability, abnormal LDL-cholesterol levels, abnormal plasma total-apolipoprotein B levels, atherosclerosis and coronary heart disease. In a particular embodiment, the individual is an individual at risk for development of disorders of lipid metabolism. In another embodiment the individual exhibits clinical symptomology associated with disorders of lipid metabolism. In one embodiment, the individual has been clinically diagnosed as having one or more disorders of lipid metabolism.

In another embodiment, the invention relates to a method for predicting the likelihood that an individual will have a disorder associated with a "G" at nucleotide position 696 of the PPARα gene (or diagnosing or aiding in the diagnosis of such a disorder) comprising the steps of obtaining a DNA sample from an individual to be assessed and determining the nucleotide present at position 696 of the PPARα gene. The presence of a "G" at this position indicates that the individual has a greater likelihood of having a disorder associated therewith than an individual having a "C" at that position, or a greater likelihood of having more severe symptomology. Conversely, the presence of a "C" at this position indicates that the individual has a lower likelihood of having a disorder associated therewith than an individual having a "G" at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of such a disorder.

In another embodiment, the invention relates to a method for predicting the likelihood that an individual will have a disorder associated with a "C" at nucleotide position 696 of the PPARα gene (or diagnosing or aiding in the diagnosis of such a disorder) comprising the steps of obtaining a DNA sample from an individual to be assessed and determining the nucleotide present at position 696 of the PPARα gene. The presence of a "C" at this position indicates that the individual has a greater likelihood of having a disorder associated therewith than an individual having a "G" at that position, or a greater likelihood of having more severe symptomology. Conversely, the presence of a "G" at this position indicates that the individual has a lower likelihood of having a disorder associated therewith than an individual having a "G" at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of such a disorder.

In another embodiment, the invention relates to a method for predicting the likelihood that an individual will have a disorder associated with an "A" at nucleotide position 971 of the PPARα gene (or diagnosing or aiding in the diagnosis of such a disorder) comprising the steps of obtaining a DNA sample from an individual to be assessed and determining the nucleotide present at position 971 of the PPARα gene. The presence of an "A" at this position indicates that the individual has a greater likelihood of having a disorder associated therewith than an individual having a "G" at that position, or a greater likelihood of having more severe symptomology. Conversely, the presence of a "G" at this position indicates that the individual has a lower likelihood of having a disorder associated therewith than an individual having a "A" at that position, or a greater likelihood of having less severe symptomology. In a particular embodiment, the individual is an individual at risk for development of such a disorder.

In another embodiment, the invention relates to a method for predicting the likelihood that an individual will have a disorder associated with a "G" at nucleotide position 971 of the PPARα gene (or diagnosing or aiding in the diagnosis of such a disorder) comprising the steps of obtaining a DNA sample from an individual to be assessed and determining the nucleotide present at position 971 of the PPARα gene. The presence of a "G" at this position indicates that the individual has a greater likelihood of having a disorder associated therewith than an individual having a "A" at that position, or a greater likelihood of having more severe symptomology. Conversely, the presence of an "A" at this position indicates that the individual has a lower likelihood of having a disorder associated therewith than an individual having a "G" at that position, or a greater likelihood of having less severe symptomology. In a particular embodiment, the individual is an individual at risk for development of such a disorder.

The genetic material to be assessed can be obtained from any nucleated cell from the individual. For assay of genomic DNA, virtually any biological sample (other than pure red blood cells) is suitable. For example, convenient tissue samples include whole blood, semen, saliva, tears, urine, fecal material, sweat, skin and hair. For assay of cDNA or mRNA, the tissue sample must be obtained from an organ in which the target nucleic acid is expressed. For example, cells from tissues that have a relatively high level of fatty acid catabolism (such as cells of the liver, kidney, heart and muscle) are suitable sources for obtaining cDNA for the PPARα gene.

Many of the methods described herein require amplification of DNA from target samples. This can be accomplished by e.g., PCR. See generally *PCR Technology: Principles and Applications for DNA Amplification* (ed. H. A. Erlich, Freeman Press, N.Y., N.Y., 1992); *PCR Protocols: A Guide to Methods and Applications* (eds. Innis. et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., Science 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The nucleotide which occupies the polymorphic site of interest (e.g., the first nucleotide in codon 162 of PPARα) can be identified by a variety methods, such as Southern analysis of genomic DNA; Northern analysis of RNA; denaturing high pressure liquid chromatography (DHPLC); gene isolation and sequencing; hybridization of an allele-specific oligonucleotide with amplified gene products; single base extension (SBE); or analysis of the PPARα protein. In a preferred embodiment, determination of the allelic form of PPARα is carried out using SBE-FRET methods, or using chip-based oligonucleotide arrays. A sampling of suitable procedures is discussed below in turn.

1. Allele-Specific Probes

The design and use of allele-specific probes for analyzing polymorphisms is described by e.g., Saiki et al., *Nature* 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some examples of which are described in WO 95/11995. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles. except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarity. See Gibbs, *Nucleic Acid Res.* 17, 2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

4. Direct-Sequencing

The direct analysis of the sequence of polymorphisms of the present invention can be accomplished using either the dideoxy chain termination method or the Maxam-Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification*, (W.H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

7. Single-Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., (*PNAS* 94:10756–61 (1997), incorporated herein by reference) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

The variant allele described herein may contribute to the bias of an individual toward disorders of lipid metabolism in one or more different ways. The polymorphism may contribute to phenotype by affecting protein structure as a result of the alteration in amino acid sequence. The polymorphism may exert phenotypic effects indirectly via influence on replication, transcription, and translation. More than one phenotypic trait may be affected. For example, other disorders which are related to disorders of lipid metabolism may also be affected by the PPARα polymorphism described herein. The polymorphism may also alter the interaction of the gene or gene product with drugs which normally interact directly with PPARα (e.g., fibrates and other drugs which affect lipid metabolism). Additionally, the described polymorphism may predispose an individual to a distinct mutation that is causally related to a certain phenotype, such as susceptibility or resistance to disorders of lipid metabolism. The discovery of the polymorphism and its correlation with disorders of lipid metabolism facilitates biochemical analysis of the variant and the development of assays to characterize the variant and to screen for pharmaceuticals that interact directly with one or another form of the protein.

Alternatively, this particular polymorphism may be one of a group of two or more polymorphisms in the PPARα gene which contributes to the presence, absence or severity of the disorder of lipid metabolism. An assessment of other polymorphisms within the gene can be undertaken, and the separate and combined effects of these polymorphisms on the disorder phenotype can be assessed.

Correlation between a particular phenotype, e.g., the high LDL-cholesterol phenotype, and the presence or absence of a particular allele is performed for a population of individuals who have been tested for the presence or absence of the phenotype. Correlation can be performed by standard statistical methods such as a Chi-squared test and statistically significant correlations between polymorphic form(s) and phenotypic characteristics are noted.

This correlation can be exploited in several ways. In the case of a strong correlation between a particular polymorphic form, e.g., the variant allele for PPARα, and a disorder for which treatment is available, detection of the polymorphic form in an individual may justify immediate administration of treatment, or at least the institution of regular monitoring of the individual. Detection of a polymorphic form correlated with a disorder in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic form and a particular disorder, immediate therapeutic intervention or monitoring may not be justified. Nevertheless, the individual can be motivated to begin simple life-style changes (e.g., diet, therapy or counseling) that can be accomplished at little cost to the individual but confer potential benefits in reducing the risk of conditions to which the individual may have increased susceptibility by virtue of the particular allele.

Furthermore, identification of a polymorphic form correlated with enhanced receptiveness to one of several treatment regimes for a disorder indicates that this treatment regime should be followed for the individual in question.

Furthermore, it may be possible to identify a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., *Proc. Natl. Acad. Sci.* (USA) 83, 7353–7357 (1986); Lander et al., *Proc. Natl. Acad. Sci.* (USA) 84, 2363–2367 (1987); Donis-Keller et al., Cell 51, 319–337 (1987); Lander et al., *Genetics* 121, 185–199 (1989)). Genes localized by linkage can be cloned by a process known as directional cloning. See Wainwright, *Med. J Australia* 159, 170–174 (1993); Collins, *Nature Genetics* 1, 3–6 (1992).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., *Science* 245, 1073–1080 (1989); Monaco et al., *Nature* 316, 842 (1985); Yamoka et al., *Neurology* 40, 222–226 (1990); Rossiter et al., *FASEB Journal* 5, 21–27 (1991).

Linkage is analyzed by calculation of LOD (log of the odds) values. A lod value is the relative likelihood of obtaining observed segregation data for a marker and a genetic locus when the two are located at a recombination fraction θ, versus the situation in which the two are not linked, and thus segregating independently (Thompson & Thompson, *Genetics in Medicine* (5th ed, W. B. Saunders Company, Philadelphia, 1991); Strachan, "Mapping the human genome" in The Human Genome (BIOS Scientific Publishers Ltd, Oxford), Chapter 4). A series of likelihood ratios are calculated at various recombination fractions (θ), ranging from θ=0.0 (coincident loci) to θ=0.50 (unlinked). Thus, the likelihood at a given value of θ is: probability of data if loci linked at θ to probability of data if loci unlinked. The computed likelihoods are usually expressed as the $\log_{10}$ of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of θ (e.g., LIPED, MLENK (Lathrop, *Proc. Nat. Acad. Sci.* (USA) 81, 3443–3446 (1984)). For any particular lod score, a recombination fraction may be determined from mathematical tables. See Smith et al., *Mathematical tables for research workers in human genetics* (Churchill, London, 1961); Smith, *Ann. Hum. Genet.* 32, 127–150 (1968). The value of θ at which the lod score is the highest is considered to be the best estimate of the recombination fraction.

Positive lod score values suggest that the two loci are linked, whereas negative values suggest that linkage is less likely (at that value of θ) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of −2 or less is taken as definitive evidence against linkage of the two loci being compared. Negative linkage data are useful in excluding a chromosome or a segment thereof from consideration. The search focuses on the remaining non-excluded chromosomal locations.

The invention further relates to isolated proteins or polypeptides comprising all or a portion of the variant amino acid sequence of PPARα (e.g., wherein reference or wild-type PPARα is exemplified by SEQ ID NO: 2; FIG. 3), and to isolated proteins or polypeptides comprising all or a portion of the variant amino acid sequence of PPARα. Preferred polypeptides are at least 10 contiguous amino acids and comprise the polymorphic amino acid, e.g., a portion of SEQ ID NO: 2 which is at least 10 contiguous amino acids and comprises the valine at residue 162. The invention further relates to isolated nucleic acid molecules encoding such proteins and polypeptides. In addition, the present invention includes biologically active fragments of the polypeptides, or analogs thereof, including organic molecules which simulate the interactions of the peptides. Biologically active fragments include any portion of the full-length polypeptide which confers a biological function on the gene product, including ligand binding, and antibody binding. Ligand binding includes binding by nucleic acids, proteins or polypeptides, small biologically active molecules, or large cellular structures.

In one embodiment, the invention relates to a method for predicting the likelihood that an individual will have a disorder of lipid metabolism (or diagnosing or aiding in the diagnosis of a disorder of lipid metabolism), e.g., high LDL cholesterol levels, atherosclerosis, coronary heart disease and/or hyperapobetalipoproteinemias, comprising the steps of obtaining a biological sample comprising the PPARα protein or relevant portion thereof from an individual to be assessed and determining the amino acid present at amino acid position 162 of the PPARα protein. The presence of a leucine (the reference amino acid) at this position indicates that the individual has a lower likelihood of having a disorder of lipid metabolism than an individual having a valine at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of a disorder of lipid metabolism.

In another embodiment, the invention relates to a method for predicting the likelihood that an individual will have a disorder of lipid metabolism (or diagnosing or 20 aiding in the diagnosis of a disorder of lipid metabolism), e.g., high LDL cholesterol levels, atherosclerosis, coronary heart disease and/or hyperapobetalipoproteinemias, comprising the steps of obtaining a.biological sample comprising the PPARα protein or relevant portion thereof from an individual to be assessed and determining the amino acid present at amino acid position 162 of the PPARα protein. The presence of a valine (the variant amino acid) at this position indicates that the individual has a greater likelihood of having a disorder of lipid metabolism than an individual having a leucine at that position, or a greater likelihood of having more severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of a disorder of lipid metabolism.

In another embodiment, the invention relates to a method for predicting the likelihood that an individual will have a disorder associated with a valine at amino acid position 162 of the PPARα protein (or diagnosing or aiding in the diagnosis of such a disorder) comprising the steps of obtaining a biological sample comprising the PPARα protein or relevant portion thereof from an individual amino acid present at amino acid position 162 of the PPARα protein. The presence of a valine at this position indicates that the individual has a greater likelihood of having a disorder associated therewith than an individual having a leucine at that position, or a greater likelihood of having more severe symptomology. Conversely, the presence of a leucine at this position indicates that the individual has a lower likelihood of having a disorder associated therewith than an individual having a valine at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of such a disorder.

In another embodiment, the invention relates to a method for predicting the likelihood that an individual will have a disorder associated with a leucine at amino acid position 162 of the PPARα protein (or diagnosing or aiding in the diagnosis of such a disorder) comprising the steps of obtaining a biological sample comprising the PPARα protein or relevant portion thereof from an individual amino acid present at amino acid position 162 of the PPARα protein. The presence of a leucine at this position indicates that the individual has a greater likelihood of having a disorder associated therewith than an individual having a valine at that position, or a greater likelihood of having more severe symptomology. Conversely, the presence of a valine at this position indicates that the individual has a lower likelihood of having a disorder associated therewith than an individual having a leucine at that position, or a greater likelihood of having less severe symptomology. In a preferred embodiment, the disorder is high LDL cholesterol levels, atherosclerosis and/or coronary heart disease. In another embodiment, the disorder is a hyperapobetalipoproteinemia. In a particular embodiment, the individual is an individual at risk for development of such a disorder.

In these embodiments of the invention, the biological sample contains protein molecules from the test subject. The term "relevant portion" of the protein is intended to mean that the portion of the protein contains the relevant amino acid position to be analysed. In vitro techniques for detection of protein include enzyme linked immunosorbent assays (ELISAs), Western blots, immunoprecipitations and immunofluorescence. Furthermore, in vivo techniques for detection of protein include introducing into a subject a labeled anti-protein antibody. For example, the antibody can be labeled with a radioactive marker whose presence and location in a subject can be detected by standard imaging techniques. Polyclonal and/or monoclonal antibodies that specifically bind to variant gene products but not to corresponding reference gene products, and vice versa, are also provided. Antibodies can be made by injecting mice or other animals with the variant gene product or synthetic peptide fragments thereof comprising the variant portion. Monoclonal antibodies are screened as are described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

Polyclonal and/or monoclonal antibodies that specifically bind to variant gene products but not to corresponding reference gene products, or to reference gene products and not to corresponding variant gene products, are also provided. Antibodies can be made by injecting mice or other animals with the variant gene product or synthetic peptide fragments thereof comprising the variant portion. Monoclonal antibodies are screened as are described, for example, in Harlow & Lane, *Antibodies, A Laboraton, Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

The invention further pertains to compositions, e.g., vectors, comprising a nucleotide sequence encoding the reference or variant gene product. For example, variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like. It is also contemplated that cells can be engineered to express the variant or reference allele of the invention by gene therapy methods. For example, DNA encoding the reference PPARα gene product, or an active fragment or derivative thereof, can be introduced into an expression vector, such as a viral vector, and the vector can be introduced into appropriate cells in an animal. In such a method, the cell population can be engineered to inducibly or constitutively express active PPARα gene product. In a preferred embodiment, the vector is delivered to the bone marrow, for example as described in Corey et al. (*Science* 244:1275–1281 (1989)).

The invention further provides transgenic nonhuman animals capable of expressing an exogenous reference or variant PPARα gene and/or having one or both alleles of an endogenous PPARα gene inactivated. Expression of an exogenous variant gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous variant genes can be achieved by forming a transgene in which a cloned variant gene is inactivated by insertion of a positive selection marker. See Capecchi, *Science* 244, 1288–1292 (1989). The transgene is then introduced into an embryonic stem cell, where it undergoes homologous recombination with an endogenous variant gene. Mice and other rodents are preferred animals. Such animals provide useful drug screening systems.

In another embodiment, the invention relates to pharmaceutical compositions comprising a reference PPARα gene product. As used herein, a reference PPARα. gene product is intended to mean functional gene products which are encoded by the reference allele of the PPARα gene. The invention further relates to the use of compositions (i.e., agonists) which enhance or increase the activity of a peptide comprising the reference PPARα gene product, or a functional portion thereof, for use in the treatment of disorders of lipid metabolism. The invention also relates to the use of compositions (i.e., antagonists) which reduce or decrease the activity of a peptide comprising the variant PPARα gene product, or a functional portion thereof, for use in the treatment of disorders of lipid metabolism.

For instance, the polypeptide or protein, or fragment thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to those skilled in the art and will depend on the ultimate pharmaceutical formulation desired. Methods of introduction of exogenous peptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents and treatment regimens.

A non-limiting description of preferred embodiments of the invention follows.

EXAMPLES

Methods

Subjects: Two independently recruited cohorts of unrelated adult Caucasians from the Quebec City area and the Saguenay-Lac-St-Jean (SLSJ) region were used to test the hypothesis that genetic variation in PPARαmay be associated with the development of dyslipidemia.

Type 2 diabetes case-control SLSJ cohort: All individuals included in this cohort are of French Canadian descent above the age of 18 years and were recruited by the Chicoutimi Hospital Lipid Clinic because they presented a family history of dyslipidemia or diabetes mellitus. These participants had previously received a family code which assured the inclusion in the present study of only one patient per pedigree in order to control for potential inflation of statistical significance due to lack of independence of observations (12). One hundred and twenty-one unrelated patients who received a new diagnosis of type 2 diabetes following an oral glucose tolerance test (OGTT) (67 men and 54 women; diabetic group), were age and sex-matched (1:1) with a patient having a normal OGTT (control group). Type 2 diabetes was defined according to the World Health Organization criteria as a 2-hour glucose concentration >11.1 mmol/L after a 75 g oral glucose absorption, whereas subjects were included in the control group when they had a 2-hour glucose concentration below 7.8 mmol/L (13). Patients diagnosed with type 2 diabetes received dietary counseling according to the American Diabetes Association. Subjects with familial hyperchylomicronemia due to mutations in the lipoprotein lipase gene were excluded from the present study. Subjects were screened for the presence of LDL-receptor gene mutations that cause familial hypercholesterolemia (FH) among French-Canadians. FH screening included two deletions (5 kb and >15 kb) and point mutations W66G, E207K, C646Y, Y268X and R329X(14–16). Waist and hip circumferences were assessed following the procedures recommended by the Airlie Conference (17). Body weight and height were also recorded, and the BMI was calculated in kg/m$^2$. Medication-free lipoprotein profiles were obtained for each subject enrolled in this study. Total-cholesterol, LDL-cholesterol, HDL-cholesterol, total-apolipoprotein B levels and plasma triglyceride concentrations were measured as previously described (18). Biological and lifestyle variables as well as medical and nutritional histories were obtained through questionnaires and physical exams performed at the Chicoutimi Hospital Lipid Clinic by trained nurses, dieticians and physicians. Smoking habits were classified as follows: 1) patients who never smoked; and 2) patients who ever smoked. Alcohol consumption was treated in two categories: 1) regular drinkers (>5 ounces of absolute alcohol/week); and 2) non-regular drinkers. A subject was considered as hypertensive when diagnosis of essential hypertension had been previously established or when three values of systolic >140 mmHg or diastolic >90 mmHg blood pressure had been recorded in the patient's medical chart. This project has been approved by the Chicoutimi Hospital Ethic Committee.

Quebec City non-diabetic male cohort: This cohort included 193 men who were recruited from the Quebec City area by solicitation through the media and were selected to cover a wide range of visceral adipose tissue accumulation. All subjects were sedentary, non-smokers and free from metabolic disorders requiring treatment such as diabetes, hypertension and coronary heart disease. A high alcohol consumption was also an exclusion criteria. BMI and waist circumference were measured as described above. Blood samples were obtained after an overnight fast from an antecubital vein. Cholesterol and triglyceride concentrations in plasma and lipoprotein fractions were enzymatically measured on an Analyzer Technicon RA-500 (Bayer Corporation, Tarry Town, N.Y.). VLDL (d<1.006 g/ml) were isolated by ultracentrifugation (19) and the HDL fraction was obtained after precipitation of LDL in the infranatant (d>1.006 g/ml) with heparin and MnCn$_2$ (20). The cholesterol content of HDL$_2$-chol and HDL$_3$-chol subfractions prepared by a precipitation method was also determined (21). HDL-apoAI was measured in the infranatant (d>1.006 g/ml) by the rocket immunoelectrophoretic method of Laurell as previously described (22). The serum standards were prepared in the laboratory, calibrated against reference sera from the Centers for Disease Control (Atlanta, Ga.), lyophilized, and stored at -85° C. until use. Coefficients of variation for repeated measurements of HDL-cholesterol and apoAI concentrations were 3.3 and 3.4%, respectively. Genomic structure of the PPARα gene: In order to design intronic primers for the amplification of each exon, genomic sequences were sought for the intronic regions surrounding all PPARα exons. To do so, the mRNA sequence of PPARα (23) was compared with a contiguous genomic DNA region taken from sequences of three overlapping clones from GenBank (Accession number: Z94161.5, AL049856, AL07861 1). Intronic primers were then designed using the Primer 3.0 software available on the Whitehead Institute/ MIT Center for Genome Research server (http:// www.genome.wi.mit.edu/cgi-bin/primer/primer3.cgi).

PCR amplification of PPARα exons and sequencing: All exons and exon-intron boundaries were amplified from genomic DNA by use of specific primers derived from the 5' and 3' intronic sequences (Table 1). The annealing temperature for all primer pairs was 59° C. PCR conditions were as follows: reaction volume was of 50 μl, 1.25 unit AmpliTaq Gold polymerase (Perkin-Elmer Cetus) in the buffer recommended by the manufacturer; 2.5 mM MgCl$_2$; 0.2 mM dNTPs; primers at a final concentration of 0.5 μM and 100 ng of template genomic DNA. PCR products were purified with magnetic beads BioMag DNA Sep (PerSeptive Biosystems, Framingham, Mass.). Sequencing reactions were performed using BigDye Primer Cycle sequencing ready reactions –21M13 kit (PE Applied BioSystems, Foster City, Calif.) and were analyzed on an ABI 377 automated sequencer (PE Applied BioSystems, Foster City, Calif.). The gel files were processed using the Sequencing analysis software (PE Applied BioSystems, Foster City, Calif.).

Detection of the L162V by polymerase chain reaction, restriction fragment length polymorphism (PCR-RFLP): The L162V mutation is caused by a C-G transversion at nucleotide 484 in exon 5. It does not alter any restriction site; thus, mismatch PCR approach was performed with the following primers Ex5.F(2) 5' GACTCAAGCTGGTGTATGACAAGT-3' (SEQ ID NO: 3) and Ex5.R-mismatch 5'-CGTTGTGTGACATCCCGACAGAAT-3' (SEQ ID NO: 4). PCR conditions were as described above. PCR products were digested with Hinfi, electrophoresed on either 12% acrylamide or 4% agarose gel and stained with ethidium bromide.

Statistical analysis: Allelic frequencies were compared using Chi-square analyses. Differences between genotypic groups were tested for statistical significance by using Student's test, and as indicated in Tables 4 and 5, some variables were log$_{10}$ transformed in order to normalize their distributions. Before performing statistical analyses on lipoprotein-lipid variables of the type 2 diabetes case-control cohort, 27 heterozygous FH subjects were excluded. Analysis of covariance was used to adjust lipid, lipoprotein and apolipoprotein variables for age alone or for both age and BMI or age and waist circumference. All statistical analyses were performed using SPSS package (SPCC Inc.) or JMP statistical package from SAS institute.

Results

Structure of the human PPARα gene: The structural organization of the gene was determined by comparing the human PPARα mRNA sequence with genomic sequences obtained from overlapping clones (FIG. 1). All 5' donor and 3' acceptor splice sites were found to obey the gt . . . ag rule (Table 2). Furthermore, all exon-intron boundaries were confirmed by direct sequencing of each exon using primers derived from intronic sequences. The human PPARα gene spans approximately 83.7 Kb. As it is the case for the mouse, human PPARα gene mRNA is composed of 8 exons, with a 5' untranslated region encoded by exons 1, 2 and part of exon 3. The coding region of PPARα is comprised within the remaining 6 exons. Intron lengths vary from 1.4 to 24.8 Kb as indicated in FIG. 1.

Identification of polymorphisms in the human PPARα gene: All exons and the exon-intron splicing boundaries of PPARα were screened by sequencing 12 patients who have been diagnosed with type 2 diabetes and 2 controls. All the amplified fragments of the PPARα gene showed the expected length, suggesting the absence of deletions, duplications or rearrangements within these fragments. Two polymorphisms were discovered within the exons. Based on the predicted amino acid sequence for this gene, the polymorphism in exon 7 is silent, with a G to A substitution which does not alter the threonine at codon 253. A new polymorphism was discovered in exon 5, which results in a L162V missense mutation. Specifically, the C to G transversion in the first position of codon 162 leads to a substitution of a valine for a leucine.

Genotype determination of the L162V mutation: A rapid screening test was developed using the mismatch PCR approach to genotype the L162V polymorphism. Using the primers Ex5R-mismatch and Ex5.F(2) described in the methods, PCR products from the mutant allele contain an HinfI restriction site that is abolished in the presence of the C at position 484. After digestion with HinjI, the PCR product from the normal allele results in a 117 bp fragment, whereas it is cleaved into 93 bp and 24 bp fragments with the mutant allele. Genotypes obtained by the mismatch PCR approach and by direct sequencing of exon 5 were in perfect agreement. Moreover, genotypes obtained by the mismatch PCR approach were repeated for a minimum of 60 randomly chosen individuals, and the reproducibility was 100%.

Association between the L162V missense mutation and lipoprotein-lipid concentrations: Chi-square analysis performed independently within the SLSJ control and diabetic groups revealed that confounding factors such as the smoking status. alcohol consumption and the use of beta-blockers or diuretic drugs as well as the prevalence of hypertension were similar between the two PPARα genotypic groups.

Furthermore, since patients have been assigned to the diabetic or control group after the OGTT, medication-free lipoprotein-lipid profile as well as fasting blood glucose and insulin levels obtained at the OGTT are shown. Subjects' characteristics according to the L162V genotype are shown in Table 4. Since mutations in the LDL-receptor gene that cause FH have a dramatic effect on the lipoprotein concentrations, heterozygous FH subjects were excluded prior to statistical analyses. Carriers of the rare V162 and L 162 homozygotes had similar fasting glucose and insulin levels as well as plasma HDL-cholesterol concentrations, independent of their clinical status: diabetic or control. Although, both diabetics and controls tended to have higher LDL-cholesterol and total-apolipoprotein B levels when they were carriers of the V162 allele, the difference did not reach statistical significance. After adjustments for co-variates such as age and/or BMI, results remained unchanged.

Although not significant, the 9% increase in plasma LDL-cholesterol levels observed among V162 carriers encouraged further investigation of the effect of that missense mutation in a larger cohort. For this purpose, a cohort of 193 non-diabetic males recruited in the greater Quebec City area were screened and for whom a more detailed lipoprotein-lipid profile was obtained. Furthermore, these subjects were free of metabolic disorders requiring treatment such as type 2 diabetes, hypertension or coronary heart disease. In the Quebec City non-diabetic male cohort, the frequency of the rare V162 allele was 6.6% (Table 3). Comparison of the lipoprotein lipid profile between the two genotypic groups showed that as in the diabetes case-control cohort, subjects carrying the rare V162 allele had higher LDL-cholesterol, LDL-apolipoprotein B and total-apolipoprotein B levels than L162 homozygotes, and these differences reach statistical significance (Table 5). Importantly, these differences remained significant after adjustments for age and BMI or for age and waist circumference.

While this invention has been particularly shown and described with references to preferred embodiments thereof, it will be understood by those skilled in the art that various changes in form and details may be made therein without departing from the scope of the invention encompassed by the appended claims.

TABLE 1

PCR primers for genomic amplification of PPARα exons.

| Exons | Oligonucleotides | | Product size | SEQ ID NO: |
|---|---|---|---|---|
| Ex. 1 | PPARαex1.F | 5'-TGTAAAACGACGGCCAGTCCATCTGGAAACAGTAAATTAAACC-3' | 169 bp | 5 |
| | PPARαex1.R | 5'-GCATCCAGAGAACAACCGTAA-3' | | 6 |
| Ex. 2 | PPARαex2.F | 5'-TGTAAAACGACGGCCAGTTAATGATAACAGAATTCATCCACCA-3' | 213 bp | 7 |
| | PPARαex2.R | 5'-TCCATTCAAGCTGCTATAACAAAAT-3' | | 8 |
| Ex. 3 | PPARαex3.F | 5'-TGTAAAACGACGGCCAGTCGTCAGTCTTACCAATTGTTCCT-3' | 311 bp | 9 |
| | PPARαex3.R | 5'-AAACTTTCTAGGAAACGGCACA-3' | | 10 |
| Ex. 4 | PPARαex4.F | 5'-TGTAAAACGACGGCCAGTCGTATGCGAAATCACATCCTC-3' | 300 bp | 11 |
| | PPARαex4.R | 5'-TAAGTAGTTGATGGTGGCGG-3' | | 12 |
| Ex. 5 | PPARαex5.F | 5'-TGTAAAACGACGGCCAGTAGTAAAGCAAGTGCGCTGGT-3' | 243 bp | 13 |
| | PPARαex5.R | 5'-AAGGAAGGGGAACTGAGGAA-3' | | 14 |
| Ex. 6 | PPARαex6.F | 5'-TGTAAAACGACGGCCAGTCTCACTGCTCATGCCTGTGT-3' | 274 bp | 15 |
| | PPARαex6.R | 5'-CCAAGAGAACCCAGAACAGC-3' | | 16 |
| Ex. 7 | PPARαex7.F | 5'-TGTAAAACGACGGCCAGTGCATCCCACATCACCTGAC-3' | 530 bp | 17 |
| | PPARαex7.R | 5'-TCAGTGACATGATACCAGCAGA-3' | | 18 |
| Ex. 8 | PPARαex8.F | 5'-TGTAAAACGACGGCCAGTTGATAAGCAGTTCTTGGGTGA-3' | 566 bp | 19 |
| | PPARαex8.R | 5'-ACCATTGAGCATAATTCGCC-3' | | 20 |

M13 tail inserted into forward primers is indicated in bold.

TABLE 2

Exon-Intron splicing boundaries.

| Exon (bp) | Donor ... Acceptor | Exon |
|---|---|---|
| exon 1 (87) | CAG:glaa ... acag:TTC | exon 2 |
| exon 2 (84) | GAG:glac ... ccag:TAG | exon 3 |

TABLE 2-continued

Exon-Intron splicing boundaries.

| Exon (bp) | Donor . . . Acceptor | Exon |
|---|---|---|
| exon 3 (250) | CGG:glaa . . . ccag:ACA | exon 4 |
| exon 4 (161) | AAG:glag . . . acag:GGC | exon 5 |
| exon 5 (139) | ACG:glag . . . clag:CGA | exon 6 |
| exon 6 (203) | CCA:glag . . . glag:CCT | exon 7 |
| exon 7 (448) | GAG:glga . . . clag:ATC | exon 8 |
| exon 8 (480) | TACTGAglic | |

Nucleotides in exons are indicated in uppercase letters, whereas the flanking nucleotides in introns are in lower case. The exact length in base pairs of the exons is indicated in parenthesis.

TABLE 3

PPARα allele frequencies.

| Population | L162 | V162 |
|---|---|---|
| Study sample #1 from SLSJ | | |
| Diabetic patients | 213 (88.0%) | 29 (12.0%) |
| Non-diabetic patients | 211 (87.2%) | 31 (12.8%) |
| Study sample #2, Quebec city non-diabetic men | 370 (93.4%) | 26 (6.6%) |

Number of alleles and percentage in parenthesis.

TABLE 4

Subjects' characteristics according to the L162V genotype in the study sample #1 of type 2 diabetic/non-diabetic patients.

| | Cases | | | Controls | | |
|---|---|---|---|---|---|---|
| Variable | L/L[1] | L/V[†2] | p-value | L/L[3] | L/V[4] | p-value |
| Age, years | 53.7 ± 6.7 (85) | 53.5 ± 8.0 (26) | 0.87 | 52.5 ± 8.5 (76) | 52.5 ± 5.9 (28) | 0.99 |
| BMI[+], kg/m² | 29.4 ± 4.2 (85) | 28.4 ± 5.2 (26) | 0.22 | 28.3 ± 3.8 (76) | 29.2 ± 3.7 (28) | 0.22 |
| Waist circumference, cm | 98.9 ± 11.7 (80) | 94.9 ± 11.6 (26) | 0.13 | 92.5 ± 12.1 (76) | 96.2 ± 12.3 (28) | 0.16 |
| Fasting glucose[+], mmol/L | 6.52 ± 1.95 (86) | 6.35 ± 1.16 (26) | 0.89 | 5.19 ± 0.55 (76) | 5.15 ± 0.67 (28) | 0.71 |
| Fasting Insulin[+], pmol/L | 127.8 ± 115.8 (43) | 147.0 ± 111.0 (15) | 0.44 | 140.4 ± 116.4 (49) | 120.0 ± 91.8 (18) | 0.74 |
| Total-cholesterol[+], mmol/L | 6.53 ± 1.67 (86) | 6.71 ± 1.19 (26) | 0.42 | 6.58 ± 1.43 (76) | 6.76 ± 1.59 (28) | 0.68 |
| LDL-cholesterol[+], mmol/L | 4.15 ± 1.35 (62) | 4.53 ± 0.85 (21) | 0.11 | 4.19 ± 0.99 (65) | 4.57 ± 1.47 (21) | 0.43 |
| HDL-cholesterol[+], mmol/L | 0.93 ± 0.32 (82) | 0.97 ± 0.27 (26) | 0.38 | 1.04 ± 0.38 (74) | 1.02 ± 0.39 (27) | 0.85 |
| Triglycerides[+], mmol/L | 4.19 ± 3.72 (85) | 3.37 ± 2.42 (26) | 0.38 | 2.89 ± 2.39 (76) | 3.24 ± 2.90 (28) | 0.76 |
| Total apolipoprotein B, g/L | 1.20 ± 0.22 (61) | 1.29 ± 0.21 (18) | 0.12 | 1.19 ± 0.30 (58) | 1.28 ± 0.32 (21) | 0.22 |

[+]$Log_{10}$-transformed variables. Data are means ± SD.
[†]One homozygote V/V included in the L/V group. Number of subjects is shown in parenthesis. Prior statistical analyses, FH patients were excluded. The male/female ratio was of 48/37, 14/12, 41/35 and 18/10 respectively for groups 1 through 4, group numbers are identified by superscripts.

TABLE 5

Subjects' characteristics according to the L162V genotype in the study sample #2 of non-diabetic men.

| Variable | L/L | L/V | p-value |
|---|---|---|---|
| Age, years | 41.7 ± 8.1 (172) | 44.7 ± 7.8 (26) | 0.08 |
| BMI, kg/m² | 29.9 ± 4.3 (171) | 29.1 ± 2.9 (25) | 0.36 |
| Waist circumference, cm | 101.0 ± 10.7 (171) | 99.7 ± 8.9 (26) | 0.54 |
| Fasting glucose[+], mmol/L | 5.41 ± 0.56 (170) | 5.33 ± 0.33 (26) | 0.55 |
| Fasting Insulin[+], pmol/L | 109.9 ± 83.7 (170) | 85.8 ± 42.5 (26) | 0.14 |
| Total-cholesterol, mmol/L | 5.21 ± 0.79 (169) | 5.50 ± 0.58 (25) | 0.08 |
| LDL-cholesterol, mmol/L | 3.49 ± 0.74 (169) | 3.86 ± 0.56 (25) | 0.02 |
| HDL-cholesterol[+], mmol/L | 0.93 ± 0.20 (169) | 0.91 ± 0.17 (25) | 0.70 |
| HDL$_2$-cholesterol, mmol/L | 0.26 ± 0.16 (166) | 0.27 ± 0.17 (25) | 0.78 |
| Triglycerides[+], mmol/L | 2.17 ± 1.16 (169) | 1.98 ± 0.80 (25) | 0.66 |
| Total-apolipoprotein B, g/L | 1.07 ± 0.24 (166) | 1.18 ± 0.16 (25) | 0.02 |
| LDL-apolipoprotein B, g/L | 0.94 ± 0.20 (166) | 1.05 ± 0.13 (25) | 0.01 |

[+]$Log_{10}$-transformed variables. Data are means ± SD. Number of subjects is shown in parenthesis.

REFERENCES

1. Schoonjans K, Martin G, Staels B, Auwerx J. Peroxisome proliferator-activated receptors, orphans with ligands and functions. Curr. Opin. Lipidol. 1997;8:159–166
2. Schoonjans K, Staels B, Auwerx J. Ther peroxisome proliferator activated receptors (PPARS) and their effects on lipid metabolism and adipocyte differentiation. Biochim Biophys Acta 1996;1302:93–109
3. Schoonjans K, Staels B, Auwerx J. Role of the peroxisome proliferator-activated receptor (PPAR) in mediating the effects of fibrates and fatty acids on gene expression. J Lipid Res 1996;37:907–925

4. Vidal-Puig A J, Considine R V, Jimenez-Linan M, et al. Peroxisome proliferator-activated receptor gene expression in human tissues. Effects of obesity, weight loss, and regulation by insulin and glucocorticoids. J Clin Invest 1997;99:2416–2422
5. Brun R P, Tontonoz P, Forman B M, et al. Differential activation of adipogenesis by multiple PPAR isoforms. Genes Dev. 1996;10:974–984
6. Isseman I, Green S. Activation of a member of the steroid hormone receptor superfamily by peroxisome proliferators. Nature 1990;347:645–650
7. Auboeuf D, Rieusset J, Fajas L, et al. Tissue distribution and quantification of the expression of mRNAs of peroxisome proliferator-activated receptors and liver X receptor-alpha in humans: no alteration in adipose tissue of obese and NIDDM patients. Diabetes 1997;46:1319–1327
8. Kliewer S A, Sundseth S S, Jones S A, et al. Fatty acids and eicosanoids regulate gene expression through direct interactions with peroxisome proliferator-activated receptors alpha and gamma. Proc. Natl. Acad. Sci. USA 1997;94:4318–4323
9. Inoue I, Noji S, Shen M Z, Takahashi K, Katayama S. The peroxisome proliferator-activated receptor alpha (PPAR alpha) regulates the plasma thiobarbituric acid-reactive substance (TBARS) level. Biochem. Biophys. Res. Commun. 1997;237:606–610
10. Horrobin D F. Abnormal membrane concentrations of 20 and 22-carbon essential fatty acids: a common link between risk factors and coronary and peripheral vascular disease? Prostaglandins Leukot Ess Fatty Acids. 1995;53:385–396
11. Reaven G M. Syndrome X: 6 years later. J Intern Med Suppl 1994;736:13–22:13–22
12. Gaudet D, Arsenault S, Belanger C, et al. Procedure to protect confidentiality of familial data in community genetics and genomic research (In Process Citation). Clin Genet 1999;55:259–264
13. Report on the Expert Committee on the diagnosis and classification of diabetes mellitus. Diabetes Care 1997;20:1183–1197
14. Couture P, Vohl M C, Gagne C, et al. Identification of three mutations in the low-density lipoprotein receptor gene causing familial hypercholesterolemia among French-Canadians. Hum Mutat 1997; suppl 1: s226–s231
15. Ma Y, Betard C, Roy M, Davignon J, Kessling A. Identification of a second "French Canadian" LDL receptor gene deletion and development of a rapid method to detect both deletions. Clinical Genetics 1989;36:219–228
16. Vohl M C, Couture P, Moorjani S, et al. Rapid restriction fragments analysis for screening four point mutations of the low-density lipoprotein receptor gene in French Canadians. Hum Mutat. 1995;6:243–246
17. Standardization of anthropometric measurements, In: *The Airlie (VA) Consensus Conference.*, edited by Lohman, T., Roche, A., Martorel., R. Human Kinetics Publishers, 1988;39–80
18. Gaudet D, Vohl M C, Julien P, et al. Relative contribution of low-density liproprotein receptor and lipoprotein lipase gene mutations to angiographically assessed coronary artery disease among french candians. Am J Cardiol 1998;82:299–305
19. Havel R J, Eder H A, Bragdon J H. The distribution and chemical composition of ultracentrifugally separated lipoproteins in human serum. J Clin Invest 1955;34:1345–1354
20. Burstein M, Samaille J. Serum dosage rapide du cholesterol lie aux alpha et aux beta lipoproteines du serum. Clin Chem Acta 1960;5:309
21. Gidez L I, Miller G J, Burnstein M, Slagle S, Eder H A. Separation and quantitation of subclasses of human plasma high density lipoproteins by a simple precipitation procedure. J Lipid Res. 1982;23:1206–1223
22. Laurell C B. Quantative estimation of proteins by electrophoresis in agarose gel containing antibodies. Anal Biochem 1966;15:42
23. Mukhedjee R, Jow L, Noonan D, McDonnell D P. Human and rat peroxisome proliferator activated receptors (PPARs) demonstrate similar tissue distribution but different responsiveness to PPAR activators. J Steriod Biochem Mol Biol 1994;51:157–166
24. Sher T, Yi H F, McBride O W, Gonzalez F J. cDNA cloning, chromosomal mapping, and functional characterization of the human peroxisome proliferator activated receptor. Biochem 1993;32:5598–5604
25. Gearing K L, Crickmore A, Gustafsson J A. Structure of the mouse peroxisome proliferator activated receptor alpha gene. Biochem Biophys Res Commun 1994;199:255–263
26. Tugwood J D, Aldridge T C, Lambe K G, Macdonald N, Woodyatt N J. Peroxisome proliferator-activated receptors: structures and function. Ann N Y Acad Sci 1996;804:252–65:252–265
27. Holden P R, Tugwood J D. Peroxisome proliferator-activated receptor alpha: role in rodent liver cancer and species differences. J Mol Endocrinol 1999;22:1–8
28. Castelli W P, Garrison R J, Wilson P W F, Abbot R D, Kalousdian S, Kannel W B. Incidence of coronary heart disease and lipoprotein cholesterol levels: the Framingham study. JAMA 1986;256:2835–2838
29. Castelli W P, Anderson K, Wilson P W, Levy D. Lipids and risk of coronary heart disease. The Framingham Study. Ann Epidemiol 1992;2:23–28
30. Lamarche B, Tchemof A, Mauriege P, et al. Fasting insulin and apolipoprotein B levels and low-density lipoprotein particle size as risk factors for ischemic heart disease. JAMA 1998;279:1955–1961
31. Bolibar I, Thompson S G, von Eckardstein A, Sandkamp M, Asamann G. Dose-response relationships of serum lipid measurements with the extent of coronary stenosis. Strong, independent, and comprehensive. ECAT Angina Pectoris Study Group. Arterioscler Thromb Vasc Biol 1955;15:1035–1042
32. Djouadi F, Weinheimer C J, Saffitz J E, et al. A gender-related defect in lipid metabolism and glucose homeostatis in peroxisome proliferator-activated receptor alpha-deficient mice. J Clin Invest 1998;102:1083–1091
33. Peters J M, Hennuyer N, Staels B, et al. Alterations in lipoprotein metabolism in peroxisome proliferator-activated receptor alpha-deficient mice. J Biol Chem 1997;272:27307–27312
34. Lamb R G, Koch J C, Bush S R. An enzymatic explanation of the differential effects of cleate and gemfibrozil on cultured hepatocyte triacylglycerol and phosphatidylcholine biosynthesis and secretion. Biochim Biophys Acta 1993;1165:299–305
35. Ruotolo G, Ericsson C G, Tettamanti C, et al. Treatment effects on serum lipoprotein lipids, apoliprproteins and low density lipoprotein particle size and relationships of lipoprotein variables to progression of coronary artery disease in the Bezafibrate Coronary Atherosclerosis Intervention Trail (BECAIT). J Am Coll Cardiol 1998;32:1648–1656
36. Ericcson C G, Results of the Bezafibrate Coronary Atherosclerosis Intervention Trial (BECAIT) and an update on trials now in progress. Eur Heart J 1998;19 Suppl H:H37–41: H37–H41
37. de Faire U, Ericsson C G, Grip L, Nilsson J, Svane B, Hamnsten A. Retardation of coronary atherosclerosis: the Bezafibrate Coronary Atherosclerosis Intervention Trial (BECAIT) and other angiographic trials. Cardiovasc Drugs Ther 1997;11 Suppl 1:259–63:257–263

38. Bell A R, Savory R, Horley N J, et al. Molecular basis of non-responsiveness to peroxisome proliferators: the guinea-pig PPARaplha is functional and mediates peroxisome proliferator-induced hypolipidaemia. Biochem J 1998;332:689–693

39. Gottlicher M, Widmark E, Li Q, Gustafsson J A. Fatty acids activate a chimera of the clofibric acid-activated receptor and the glucocorticoid receptor. Proc Natl Acad Sci USA 1992;89:4653–4657

What is claimed is:

1. A method for predicting the likelihood that a human will have increased LDL-cholesterol levels, increased LDL-apolipoprotein B levels and/or increased total-apolipoprotein B levels, comprising the steps of obtaining a DNA sample from a human to be assessed and determining the nucleotide present at the first position of codon 162 of the PPARα gene, wherein the presence of a C at this position indicates that the person has a lower likelihood of having increased LDL-cholesterol levels, increased LDL-apolipoprotein B levels and/or increased total-apolipoprotein B levels than a person having a G at that position.

2. A method for predicting the likelihood that a human will have increased LDL-cholesterol levels, increased LDL-apolipoprotein B levels and/or increased total-apolipoprotein B levels, comprising the steps of obtaining a DNA sample from a human to be assessed and determining the nucleotide present at the first position of codon 162 of the PPARα gene, wherein the presence of a G at this position indicates that the person has a greater likelihood of having increased LDL-cholesterol levels, increased LDL-apolipoprotein B levels and/or increased total-apolipoprotein B levels than a person having a C at that position.

3. A method for predicting the severity of symptomology associated with increased LDL-cholesterol levels, increased LDL-apolipoprotein B levels and/or increased total-apolipoprotein B levels, comprising the steps of obtaining a DNA sample from a human to be assessed and determining the nucleotide present at the first position of codon 162 of the PPARα gene, wherein the presence of a C at this position indicates that the person has a greater likelihood of having less severe symptomology associated with increased LDL-cholesterol levels, increased LDL-apolipoprotein B levels and/or increased total-apolipoprotein B levels than a person having a G at that position.

4. A method for predicting the severity of symptomology associated with increased LDL-cholesterol levels, increased LDL-apolipoprotein B levels and/or increased total-apolipoprotein B levels, comprising the steps of obtaining a DNA sample from a human to be assessed and determining the nucleotide present at the first position of codon 162 of the PPARα gene, wherein the presence of a G at this position indicates that the person has a greater likelihood of having more severe symptomology associated with increased LDL-cholesterol levels, increased LDL-apolipoprotein B levels and/or increased total-apolipoprotein B levels than a person having a C at that position.

5. A method for predicting the likelihood that a human will have at least one disorder selected from the group consisting of atherosclerosis, hyperapobetalipoproteinemia and coronary heart disease, comprising the steps of obtaining a DNA sample from a human to be assessed and determining the nucleotide present at the first position of codon 162 of the PPARα gene, wherein the presence of a C at this position indicates that the person has a lower likelihood of having atherosclerosis, hyperapobetalipoproteinemia and/or coronary heart disease than a person having a G at that position.

6. A method for predicting the severity of symptomology associated with at least one disorder selected from the group consisting of atherosclerosis, hyperapobetalipoproteinemia and coronary heart disease, comprising the steps of obtaining a DNA sample from a human to be assessed and determining the nucleotide present at the first position of codon 162 of the PPARα gene, wherein the presence of a C at this position indicates that the person has a greater likelihood of having less severe symptomology associated with atherosclerosis, hyperapobetalipoproteinemia and/or coronary heart disease than a person having a G at that position.

7. A method for predicting the likelihood that a human will have at least one disorder selected from the group consisting of atherosclerosis, hyperapobetalipoproteinemia and coronary heart disease, comprising the steps of obtaining a DNA sample from a human to be assessed and determining the nucleotide present at the first position of codon 162 of the PPARα gene, wherein the presence of a G at this position indicates that the person has a greater likelihood of having atherosclerosis, hyperapobetalipoproteinemia and/or coronary heart disease than a person having a C at that position.

8. A method for predicting the severity of symptomology associated with at least one disorder selected from the group consisting of atherosclerosis, hyperapobetalipoproteinemia and coronary heart disease, comprising the steps of obtaining a DNA sample from a human to be assessed and determining the nucleotide present at the first position of codon 162 of the PPARα gene, wherein the presence of a G at this position indicates that the person has a greater likelihood of having more severe symptomology associated with atherosclerosis, hyperapobetalipoproteinemia and/or coronary heart disease than a person having a C at that position.

* * * * *

SEQUENCE LISTING

<160> NUMBER OF SEQ ID NOS: 20

<210> SEQ ID NO 1
<211> LENGTH: 1850
<212> TYPE: DNA
<213> ORGANISM: Homo sapiens

<400> SEQUENCE: 1

| | | | | | |
|---|---|---|---|---|---|
| ggcccaggct | gaagctcagg | gccctgtctg | ctctgtggac | tcaacagttt | gtggcaagac | 60 |
| aagctcagaa | ctgagaagct | gtcaccacag | ttctggaggc | tgggaagttc | aagatcaaag | 120 |
| tgccagcaga | ttcagtgtca | tgtgaggacg | tgcttcctgc | ttcatagata | agagcttgga | 180 |
| gctcggcgca | caaccagcac | catctggtcg | cgatggtgga | cacggaaagc | ccactctgcc | 240 |
| ccctctcccc | actcgaggcc | ggcgatctag | agagcccgtt | atctgaagag | ttcctgcaag | 300 |
| aaatgggaaa | catccaagag | atttcgcaat | ccatcggcga | ggatagttct | ggaagctttg | 360 |
| gctttacgga | ataccagtat | ttaggaagct | gtcctggctc | agatggctcg | gtcatcacgg | 420 |
| acacgctttc | accagcttcg | agcccctcct | cggtgactta | tcctgtggtc | cccggcagcg | 480 |
| tggacgagtc | tcccagtgga | gcattgaaca | tcgaatgtag | aatctgcggg | gacaaggcct | 540 |
| caggctatca | ttacggagtc | cacgcgtgtg | aaggctgcaa | gggcttcttt | cggcgaacga | 600 |
| ttcgactcaa | gctggtgtat | gacaagtgcg | accgcagctg | caagatccag | aaaaagaaca | 660 |
| gaaacaaatg | ccagtattgt | cgatttcaca | agtgcctttc | tgtcgggatg | tcacacaacg | 720 |
| cgattcgttt | tggacgaatg | ccaagatctg | agaaagcaaa | actgaaagca | gaaattctta | 780 |
| cctgtgaaca | tgacatagaa | gattctgaaa | ctgcagatct | caaatctctg | gccaagagaa | 840 |
| tctacgaggc | ctacttgaag | aacttcaaca | tgaacaaggt | caaagcccgg | gtcatcctct | 900 |
| caggaaaggc | cagtaacaat | ccacctttttg | tcatacatga | tatggagaca | ctgtgtatgg | 960 |
| ctgagaagac | gctggtggcc | aagctggtgg | ccaatggcat | ccagaacaag | gaggcggagg | 1020 |
| tccgcatctt | tcactgctgc | cagtgcacgt | cagtggagac | cgtcacggag | ctcacggaat | 1080 |
| tcgccaaggc | catcccaggc | ttcgcaaact | tggacctgaa | cgatcaagtg | acattgctaa | 1140 |
| aatacggagt | ttatgaggcc | atattcgcca | tgctgtcttc | tgtgatgaac | aaagacggga | 1200 |
| tgctggtagc | gtatggaaat | gggtttataa | ctcgtgaatt | cctaaaaagc | ctaaggaaac | 1260 |
| cgttctgtga | tatcatggaa | cccaagtttg | attttgccat | gaagttcaat | gcactggaac | 1320 |
| tggatgacag | tgatatctcc | cttttttgtgg | ctgctatcat | ttgctgtgga | gatcgtcctg | 1380 |
| gccttctaaa | cgtaggacac | attgaaaaaa | tgcaggaggg | tattgtacat | gtgctcagac | 1440 |
| tccacctgca | gagcaaccac | ccggacgata | tctttctctt | cccaaaactt | cttcaaaaaa | 1500 |
| tggcagacct | ccggcagctg | gtgacggagc | atgcgcagct | ggtgcagatc | atcaagaaga | 1560 |
| cggagtcgga | tgctgcgctg | cacccgctac | tgcaggagat | ctacagggac | atgtactgag | 1620 |
| ttccttcaga | tcagccacac | cttttccagg | agttctgaag | ctgacagcac | tacaaaggag | 1680 |
| acgggggagc | agcacgattt | tgcacaaata | tccaccactt | taaccttaga | gcttggacag | 1740 |
| tctgagctgt | aggtaaccgg | catattattc | catatctttg | ttttaaccag | tacttctaag | 1800 |

-continued agcatagaac tcaaatgctg ggggaggtgg ctaatctcag gactgggaag　　　1850

<210> SEQ ID NO 2
<211> LENGTH: 468
<212> TYPE: PRT
<213> ORGANISM: Homo sapiens

<400> SEQUENCE: 2

Met Val Asp Thr Glu Ser Pro Leu Cys Pro Leu Ser Pro Leu Glu Ala
1               5                   10                  15

Gly Asp Leu Glu Ser Pro Leu Ser Glu Glu Phe Leu Gln Glu Met Gly
            20                  25                  30

Asn Ile Gln Glu Ile Ser Gln Ser Ile Gly Glu Asp Ser Ser Gly Ser
        35                  40                  45

Phe Gly Phe Thr Glu Tyr Gln Tyr Leu Gly Ser Cys Pro Gly Ser Asp
    50                  55                  60

Gly Ser Val Ile Thr Asp Thr Leu Ser Pro Ala Ser Ser Pro Ser Ser
65                  70                  75                  80

Val Thr Tyr Pro Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
        115                 120                 125

Thr Ile Arg Leu Lys Leu Val Tyr Asp Lys Cys Asp Arg Ser Cys Lys
    130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Ile Glu Asp Ser Glu Thr Ala Asp Leu Lys Ser Leu Ala Lys
        195                 200                 205

Arg Ile Tyr Glu Ala Tyr Leu Lys Asn Phe Asn Met Asn Lys Val Lys
    210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255

Lys Leu Val Ala Asn Gly Ile Gln Asn Lys Glu Ala Glu Val Arg Ile
            260                 265                 270

Phe His Cys Cys Gln Cys Thr Ser Val Glu Thr Val Thr Glu Leu Thr
        275                 280                 285

Glu Phe Ala Lys Ala Ile Pro Gly Phe Ala Asn Leu Asp Leu Asn Asp
    290                 295                 300

Gln Val Thr Leu Leu Lys Tyr Gly Val Tyr Glu Ala Ile Phe Ala Met
305                 310                 315                 320

Leu Ser Ser Val Met Asn Lys Asp Gly Met Leu Val Ala Tyr Gly Asn
                325                 330                 335

Gly Phe Ile Thr Arg Glu Phe Leu Lys Ser Leu Arg Lys Pro Phe Cys
            340                 345                 350

Asp Ile Met Glu Pro Lys Phe Asp Phe Ala Met Lys Phe Asn Ala Leu
        355                 360                 365

```
Glu Leu Asp Asp Ser Asp Ile Ser Leu Phe Val Ala Ala Ile Ile Cys
    370                 375                 380

Cys Gly Asp Arg Pro Gly Leu Leu Asn Val Gly His Ile Glu Lys Met
385                 390                 395                 400

Gln Glu Gly Ile Val His Val Leu Arg Leu His Leu Gln Ser Asn His
                405                 410                 415

Pro Asp Asp Ile Phe Leu Phe Pro Lys Leu Leu Gln Lys Met Ala Asp
            420                 425                 430

Leu Arg Gln Leu Val Thr Glu His Ala Gln Leu Val Gln Ile Ile Lys
        435                 440                 445

Lys Thr Glu Ser Asp Ala Ala Leu His Pro Leu Leu Gln Glu Ile Tyr
    450                 455                 460

Arg Asp Met Tyr
465

<210> SEQ ID NO 3
<211> LENGTH: 24
<212> TYPE: DNA
<213> ORGANISM: Artificial Sequence
<220> FEATURE:
<223> OTHER INFORMATION: primer sequence

<400> SEQUENCE: 3
gactcaagct ggtgtatgac aagt                                          24

<210> SEQ ID NO 4
<211> LENGTH: 24
<212> TYPE: DNA
<213> ORGANISM: Artificial Sequence
<220> FEATURE:
<223> OTHER INFORMATION: primer sequence

<400> SEQUENCE: 4
cgttgtgtga catcccgaca gaat                                          24

<210> SEQ ID NO 5
<211> LENGTH: 43
<212> TYPE: DNA
<213> ORGANISM: Artificial Sequence
<220> FEATURE:
<223> OTHER INFORMATION: primer sequence

<400> SEQUENCE: 5
tgtaaaacga cggccagtcc atctggaaac agtaaattaa acc                     43

<210> SEQ ID NO 6
<211> LENGTH: 21
<212> TYPE: DNA
<213> ORGANISM: Artificial Sequence
<220> FEATURE:
<223> OTHER INFORMATION: primer sequence

<400> SEQUENCE: 6
gcatccagag aacaaccgta a                                             21

<210> SEQ ID NO 7
<211> LENGTH: 43
<212> TYPE: DNA
<213> ORGANISM: Artificial Sequence
<220> FEATURE:
<223> OTHER INFORMATION: primer sequence

<400> SEQUENCE: 7
```
tgtaaaacga cggccagtta atgataacag aattcatcca cca        43

<210> SEQ ID NO 8
<211> LENGTH: 25
<212> TYPE: DNA
<213> ORGANISM: Artificial Sequence
<220> FEATURE:
<223> OTHER INFORMATION: primer sequence

<400> SEQUENCE: 8
tccattcaag ctgctataac aaaat        25

<210> SEQ ID NO 9
<211> LENGTH: 41
<212> TYPE: DNA
<213> ORGANISM: Artificial Sequence
<220> FEATURE:
<223> OTHER INFORMATION: primer sequence

<400> SEQUENCE: 9
tgtaaaacga cggccagtcg tcagtcttac caattgttcc t        41

<210> SEQ ID NO 10
<211> LENGTH: 22
<212> TYPE: DNA
<213> ORGANISM: Artificial Sequence
<220> FEATURE:
<223> OTHER INFORMATION: primer sequence

<400> SEQUENCE: 10
aaactttcta ggaaacggca ca        22

<210> SEQ ID NO 11
<211> LENGTH: 39
<212> TYPE: DNA
<213> ORGANISM: Artificial Sequence
<220> FEATURE:
<223> OTHER INFORMATION: primer sequence

<400> SEQUENCE: 11
tgtaaaacga cggccagtcg tatgcgaaat cacatcctc        39

<210> SEQ ID NO 12
<211> LENGTH: 20
<212> TYPE: DNA
<213> ORGANISM: Artificial Sequence
<220> FEATURE:
<223> OTHER INFORMATION: primer sequence

<400> SEQUENCE: 12
taagtagttg atggtggcgg        20

<210> SEQ ID NO 13
<211> LENGTH: 38
<212> TYPE: DNA
<213> ORGANISM: Artificial Sequence
<220> FEATURE:
<223> OTHER INFORMATION: primer sequence

<400> SEQUENCE: 13
tgtaaaacga cggccagtag taaagcaagt gcgctggt        38

<210> SEQ ID NO 14
<211> LENGTH: 20
<212> TYPE: DNA
<213> ORGANISM: Artificial Sequence

```
<220> FEATURE:
<223> OTHER INFORMATION: primer sequence

<400> SEQUENCE: 14
aaggaagggg aactgaggaa                                                      20

<210> SEQ ID NO 15
<211> LENGTH: 38
<212> TYPE: DNA
<213> ORGANISM: Artificial Sequence
<220> FEATURE:
<223> OTHER INFORMATION: primer sequence

<400> SEQUENCE: 15
tgtaaaacga cggccagtct cactgctcat gcctgtgt                                  38

<210> SEQ ID NO 16
<211> LENGTH: 20
<212> TYPE: DNA
<213> ORGANISM: Artificial Sequence
<220> FEATURE:
<223> OTHER INFORMATION: primer sequence

<400> SEQUENCE: 16
ccaagagaac ccagaacagc                                                      20

<210> SEQ ID NO 17
<211> LENGTH: 37
<212> TYPE: DNA
<213> ORGANISM: Artificial Sequence
<220> FEATURE:
<223> OTHER INFORMATION: primer sequence

<400> SEQUENCE: 17
tgtaaaacga cggccagtgc atcccacatc acctgac                                   37

<210> SEQ ID NO 18
<211> LENGTH: 22
<212> TYPE: DNA
<213> ORGANISM: Artificial Sequence
<220> FEATURE:
<223> OTHER INFORMATION: primer sequence

<400> SEQUENCE: 18
tcagtgacat gataccagca ga                                                   22

<210> SEQ ID NO 19
<211> LENGTH: 39
<212> TYPE: DNA
<213> ORGANISM: Artificial Sequence
<220> FEATURE:
<223> OTHER INFORMATION: primer sequence

<400> SEQUENCE: 19
tgtaaaacga cggccagttg ataagcagtt cttgggtga                                 39

<210> SEQ ID NO 20
<211> LENGTH: 20
<212> TYPE: DNA
<213> ORGANISM: Artificial Sequence
<220> FEATURE:
<223> OTHER INFORMATION: primer sequence

<400> SEQUENCE: 20
accattgagc ataattcgcc                                                      20
```